US00PP35685P2

(12) United States Plant Patent
Arts

(10) Patent No.: US PP35,685 P2
(45) Date of Patent: Mar. 12, 2024

(54) ***HYDRANGEA* PLANT NAMED 'H223906'**

(50) Latin Name: *Hydrangea macrophylla*
Varietal Denomination: H223906

(71) Applicant: HYDRANGEA BREEDERS ASSOCIATION B.V., De Kwakel (NL)

(72) Inventor: Niels Arts, Aalsmeer (NL)

(73) Assignee: HYDRANGEA BREEDERS ASSOCIATION B.V., De Kwakel (NL)

( * ) Notice: Subject to any disclaimer, the term of this patent is extended or adjusted under 35 U.S.C. 154(b) by 0 days.

(21) Appl. No.: 18/206,293

(22) Filed: Jun. 6, 2023

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — C. Anne Whealy

(57) ABSTRACT

A new and distinct cultivar of *Hydrangea* plant named 'H223906', characterized by its relatively compact, upright and uniformly mounded plant habit; vigorous growth habit and rapid growth rate; freely branching habit with strong, thick and sturdy stems; freely and uniformly flowering habit; mophead-type inflorescences with numerous sterile flowers that are yellow green and purplish red in color; and good postproduction longevity.

2 Drawing Sheets

Figure 1:
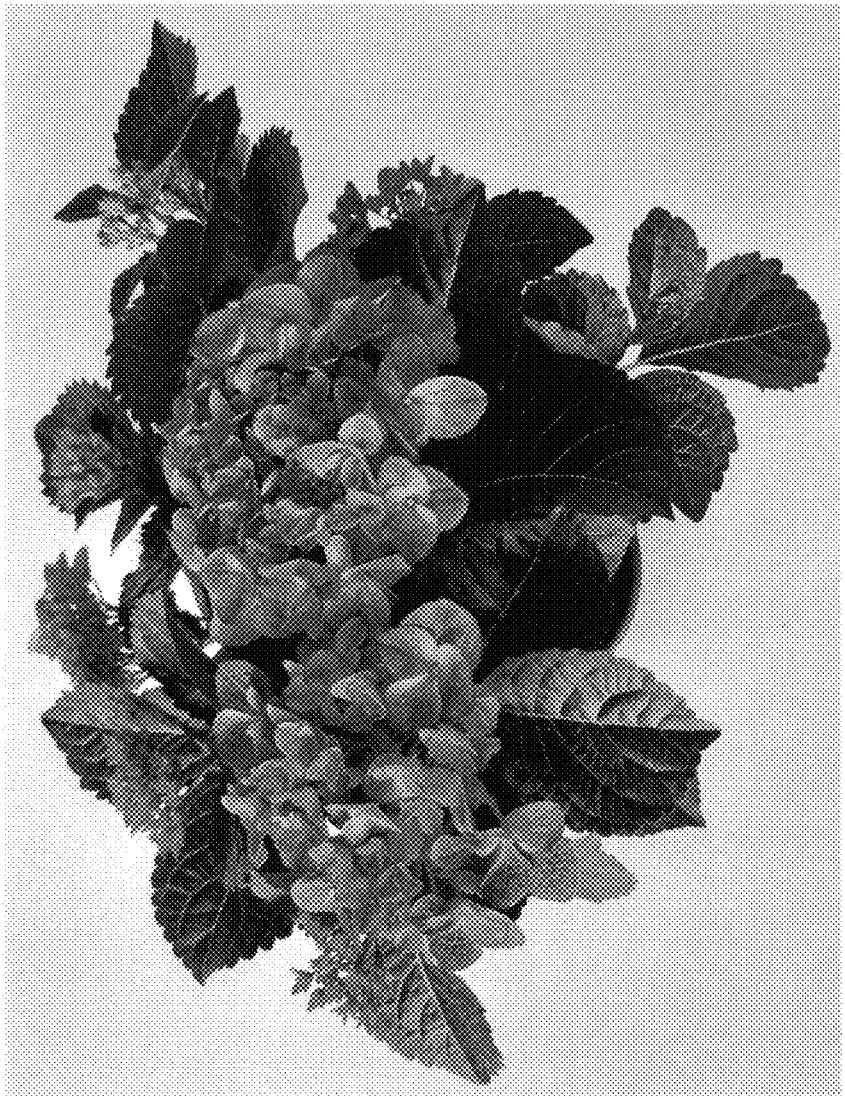

Botanical designation: *Hydrangea macrophylla.*
Cultivar denomination: 'H223906'.

CROSS-REFERENCED TO CLOSELY-RELATED APPLICATION(S)

United States Plant Patent Application:
Title: *Hydrangea* Plant Named 'H223905'
Inventor: Niels Arts
Filed: Jun. 6, 2023, application Ser. No. 18/206,293, concurrently with this application An European Community Plant Breeder's Rights application for the instant plant was filed by the Applicant/Assignee, *Hydrangea* Breeders Association B.V. of De Kwakel, The Netherlands on Mar. 9, 2023, application number 2023/0598. Foreign priority is not claimed to this application.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'H223906'.

The new *Hydrangea* plant is a product of a planned breeding program conducted by the Inventor in De Kwakel, The Netherlands and Lengerich, Germany. The objective of the breeding program was to create new strong and freely-branching *Hydrangea* plants with strong sturdy stems, uniform flowering habit, large inflorescences with numerous showy sterile flowers, attractive sterile flower color and good postproduction longevity.

The new *Hydrangea* plant originated from a cross-pollination made by the Inventor during the spring of 2017 in De Kwakel, The Netherlands, of *Hydrangea macrophylla* 'H213906', disclosed in U.S. Plant Pat. No. 26,509, as the female, or seed, parent with a proprietary selection of *Hydrangea macrophylla* identified as code number K1-17, not patented, as the male, or pollen, parent. The new *Hydrangea* plant was discovered and selected by the Inventor as a single flowering plant from within the progeny of the stated cross-pollination in a controlled greenhouse environment in Lengerich, Germany during the spring of 2019.

Asexual reproduction of the new *Hydrangea* plant by vegetative tip cuttings in a controlled environment in De Kwakel, The Netherlands since the summer of 2019 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'H223906'. These characteristics in combination distinguish 'H223906' as a new and distinct *Hydrangea* plant:

1. Relatively compact, upright and uniformly mounded plant habit.
2. Vigorous growth habit and rapid growth rate.
3. Freely branching habit with strong, thick and sturdy stems.
4. Freely and uniformly flowering habit.
5. Mophead-type inflorescences with numerous sterile flowers that are yellow green and purplish red in color.
6. Good postproduction longevity.

Plants of the new *Hydrangea* can be compared to plants of the female parent, 'H213906'. Plants of the new *Hydran-*

*gea* differ primarily from plants of 'H213906' in sterile flower color as sterile flowers of plants of the new *Hydrangea* are darker purplish red in color than plants of 'H213906'.

Plants of the new *Hydrangea* can be compared to plants of the male parent selection. Plants of the new *Hydrangea* differ primarily from plants of the male parent selection in branching habit as plants of the new *Hydrangea* are more freely branching than plants of the male parent selection. In addition, plants of the new *Hydrangea* have darker purplish red-colored sterile flowers than plants of the male parent selection.

Plants of the new *Hydrangea* can be compared to plants of the *Hydrangea macrophylla* 'H223905', disclosed in a U.S. Plant Patent application filed concurrently. In side-by-side comparisons, plants of the new *Hydrangea* differ primarily from plants of 'H223905' in the following characteristics:

1. Plants of the new *Hydrangea* are not as freely branching as plants of 'H223905'.
2. Inflorescences of plants of the new *Hydrangea* have more fertile and sterile flowers than inflorescences of plants of 'H223905'.

Plants of the new *Hydrangea* can also be compared to plants of the *Hydrangea macrophylla* '200749077', disclosed in U.S. Plant Pat. No. 16,441. In side-by-side comparisons, plants of the new *Hydrangea* differ primarily from plants of '200749077' in the following characteristics:

1. Plants of the new *Hydrangea* are broader than plants of '200749077'.
2. Plants of the new *Hydrangea* have thicker lateral branches than plants of '200749077'.
3. Plants of the new *Hydrangea* have larger leaves than plants of '200749077'.
4. Plants of the new *Hydrangea* flower later than plants of '200749077'.
5. Plants of the new *Hydrangea* have broader inflorescences than plants of '200749077'.
6. Plants of the new *Hydrangea* have larger sterile flowers than plants of '200749077'.
7. Sterile flowers of plants of the new *Hydrangea* are yellow green and purplish red in color whereas sterile flowers of plants of '200749077' are light purplish pink in color (when not "blued").

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a top perspective view of a typical flowering plant of 'H223906'.

Figure 2:
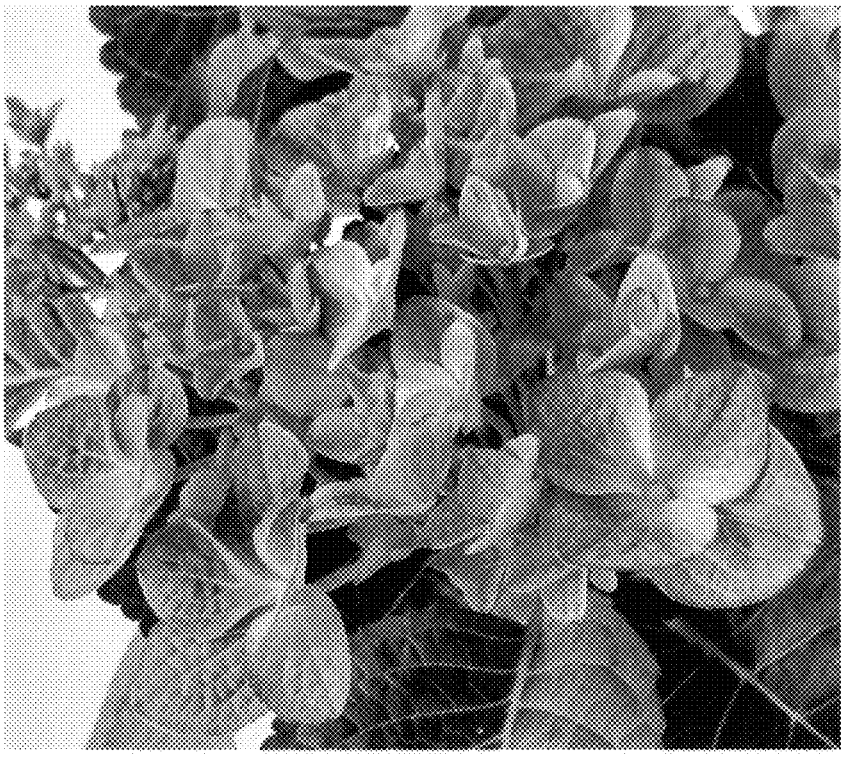

The photograph on the second sheet (FIG. 2) is a close-up view of a typical inflorescence of 'H223906'.

DETAILED BOTANICAL DESCRIPTION

Plants used in the aforementioned photographs and in the following description were grown during the spring and early summer in 17-cm containers in a glass-covered greenhouse in Lengerich, Germany and under cultural practices typical of commercial *Hydrangea* production. During the production of the plants, day and night temperatures averaged 17 C. Plants of the new *Hydrangea* were 14 months old when the photographs and description were taken. Plants of the new *Hydrangea* can be treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'H223906'.

Parentage:

*Female, or seed, parent.*—*Hydrangea macrophylla* 'H213906', disclosed in U.S. Plant Pat. No. 26,509.

*Male, or pollen, parent.*—Proprietary selection of *Hydrangea macrophylla* identified as code number K1-17, not patented.

Propagation:

*Type cutting.*—By vegetative tip cuttings.

*Time to initiate roots, summer.*—About two weeks at temperatures about 23 C.

*Time to initiate roots, winter.*—About 18 days at temperatures about 20 C.

*Time to produce a rooted young plant, summer.*—About four weeks at temperatures about 23 C.

*Time to produce a rooted young plant, winter.*—About five weeks at temperatures about 20 C.

*Root description.*—Thick; typically whitish brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Relatively compact, upright and uniformly mounded plant habit; strong and sturdy stems; rapid growth rate and vigorous growth habit.

*Plant height.*—About 25 cm.

*Plant diameter or area of spread.*—About 45 cm to 50 cm.

Lateral branch description:

*Branching habit.*—Freely branching habit; when pinched, about eight lateral branches develop per plant.

*Length.*—About 15 cm to 20 cm.

*Diameter.*—About 8 mm to 10 mm.

*Internode length.*—About 4 cm to 6 cm.

*Texture.*—Smooth, glabrous; fully developed, woody.

*Aspect.*—Upright to slightly outwardly.

*Strength.*—Strong, sturdy.

*Color.*—When developing: Close to 144A. Fully developed: Close to 177C; lenticels, close to 187A.

Leaf description:

*Arrangement.*—Opposite, simple.

*Length.*—About 13 cm to 15 cm.

*Width.*—About 9 cm to 10 cm.

*Shape.*—Ovate.

*Apex.*—Acute.

*Base.*—Obtuse.

*Margin.*—Dentate.

*Texture, upper surface.*—Smooth to rugose, glabrous.

*Texture, lower surface.*—Rugose, glabrous.

*Venation pattern.*—Pinnate.

*Color.*—Developing and fully expanded leaves, upper surface: Close to NN137A; venation, close to 144B.

Developing and fully expanded leaves, lower surface: Close to 137C; venation, close to 144B.

*Petioles*.—Length: About 2 cm to 4 cm. Diameter: About 4 mm. Texture, upper and lower surfaces: Smooth, glabrous. Color, upper and lower surfaces: Close to 144B.

Flower description:

*Flower type and habit*.—Small and inconspicuous fertile flowers and showy sterile flowers arranged on mophead-type terminal panicles; panicles upright and globular in shape; fertile flowers face upright and sterile flowers face upright to outwardly depending on their position in the inflorescence.

*Fragrance*.—None detected.

*Time to flowering*.—Plants begin flowering about eight weeks after cold treatment.

*Flower longevity*.—Fertile flowers last about three months on the plant, fertile flowers not persistent; sterile flowers last about three months on the plant, sterile flowers persistent.

*Quantity of flowers*.—Freely flowering habit; about 30 to 40 fertile flowers and about 70 sterile flowers per panicle.

*Panicle height*.—About 8 cm to 10 cm.

*Panicle diameter*.—About 20 cm.

*Fertile flower buds*.—Length: About 5 mm. Diameter: About 3 mm. Shape: Spherical. Color: Close to 144A.

*Sterile flower buds*.—Length: About 1 cm. Diameter: About 1 cm. Shape: Spherical. Color: Close to 144A.

*Fertile flower diameter*.—About 5 mm.

*Fertile flower depth* (*height*).—About 4 mm.

*Sterile flower diameter*.—About 5 cm to 7 cm.

*Sterile flower depth* (*height*).—About 1 cm.

*Petals, fertile flowers*.—Quantity and arrangement: About five in a single whorl. Length: About 4 mm. Width: About 2 mm. Shape: Ovate. Apex: Acute. Base: Obtuse. Margin: Entire. Texture, upper and lower surfaces: Smooth, glabrous. Color: When opening, upper and lower surfaces: Close to 65C. Fully opened, upper and lower surfaces: Close to 65B; color does not change with subsequent development.

*Petals, sterile flowers*.—Quantity and arrangement: About four in a single whorl. Length: About 4 mm. Width: About 2 mm. Shape: Ovate. Apex: Acute. Base: Attenuate. Margin: Entire. Texture, upper and lower surfaces: Smooth, glabrous. Color: When opening, upper and lower surfaces: Close to 145B. Fully opened, upper and lower surfaces: Close to 65A; color does not change with subsequent development.

*Sepals, fertile flowers*.—Quantity and arrangement: About five in a single whorl. Length: About 2 mm. Width: About 2 mm. Shape: Ovate. Apex: Acute. Base: Obtuse. Margin: Entire. Texture, upper and lower surfaces: Smooth, glabrous. Color: When opening, upper and lower surfaces: Close to 145A. Fully opened, upper and lower surfaces: Close to 145A; color does not change with subsequent development.

*Sepals, sterile flowers*.—Quantity and arrangement: About four in a single whorl. Length: About 3 cm to 3.5 cm. Width: About 3 cm to 3.5 cm. Shape: Deltoid. Apex: Obtuse. Base: Obtuse. Margin: Entire. Texture, upper surface: Smooth, glabrous. Texture, lower surface: Smooth to rugose, glabrous. Color: When opening, upper and lower surfaces: Center, close to 145C; towards the margins, close to 60A. Fully opened, upper and lower surfaces: Center, close to 63A; towards the margins, close to 143C; sepals becoming more predominantly purplish red with subsequent development; when "blued" with aluminum sulfate, color is close to 70A and 90B.

*Pedicels, fertile flowers*.—Length: About 5 mm to 10 mm. Diameter: About 1 mm to 2 mm. Strength: Strong. Aspect: About 45 degrees from vertical. Texture: Smooth, glabrous. Color: Close to 63C.

*Pedicels, sterile flowers*.—Length: About 4 cm. Diameter: About 2 mm. Strength: Strong. Aspect: About 45 degrees from vertical. Texture: Smooth, glabrous. Color: Close to 65D.

*Reproductive organs, fertile flowers*.—Stamens: Quantity per flower: About eight. Filament length: About 2 mm. Filament color: Close to 69D. Anther length: About 1 mm. Anther shape: Round. Anther color: Close to 69D. Pollen amount: Abundant. Pollen color: Close to 155A. Pistils: Pistil quantity per flower: One. Pistil length: About 1 mm to 2 mm. Stigma shape: Three-lobed. Stigma color: Close to 69B. Style length: About 2 mm to 3 mm. Style color: Close to 69D. Ovary color: Close to 69D.

*Reproductive organs, sterile flowers*.—Stamens: Quantity per flower: About eight. Filament length: About 2 mm. Filament color: Close to 145C. Anther length: About 2 mm. Anther shape: Conical. Anther color: Close to 145C. Pollen amount: Abundant. Pollen color: Close to 155A. Pistils: Pistil quantity per flower: One. Pistil length: About 2 mm. Stigma shape: Three-lobed. Stigma color: Close to 145A. Style length: About 2 mm. Style color: Close to 145A. Ovary color: Close to 145A.

*Seeds, only produced by fertile flowers*.—Quantity per fertile flower: About 20 to 30. Length: About 1 mm. Diameter: About 0.2 mm. Color: Close to 200C.

Pathogen & pest resistance: To date, plants of the new *Hydrangea* grown under commercial production conditions have not been observed to be resistant to pathogens and pests common to *Hydrangea* plants.

Garden performance: Plants of the new *Hydrangea* have been shown to have good garden performance and to be tolerant to temperatures ranging from about 3 C to about 38 C.

It is claimed:

1. A new and distinct *Hydrangea* plant named 'H223906' as illustrated and described.

* * * * *